United States Patent [19]

Tulip

[11] Patent Number: 6,121,627
[45] Date of Patent: Sep. 19, 2000

[54] GAS DETECTOR WITH REFERENCE CELL

[76] Inventor: John Tulip, 11625 Edinboro Rd., Edmonton, Alberta, Canada, T6G 1S2

[21] Appl. No.: 09/143,970

[22] Filed: Aug. 31, 1998

[51] Int. Cl.$^7$ ..................................................... G01V 8/00
[52] U.S. Cl. ........................ 250/559.4; 250/343; 356/437
[58] Field of Search ................................ 250/559.4, 573, 250/575, 576, 343, 564; 356/437, 318, 73; 73/23.22, 23.41

[56] References Cited

U.S. PATENT DOCUMENTS

| | | | |
|---|---|---|---|
| 3,697,185 | 10/1972 | Kassel et al. | 356/181 |
| 4,820,045 | 4/1989 | Boisde et al. | 356/319 |
| 4,968,887 | 11/1990 | Wong | 250/343 |
| 5,026,991 | 6/1991 | Goldstein et al. | 250/343 |
| 5,047,639 | 9/1991 | Wong | 250/341 |
| 5,173,749 | 12/1992 | Tell et al. | 356/437 |
| 5,202,570 | 4/1993 | Tanaka et al. | 250/575 |
| 5,301,014 | 4/1994 | Koch | 356/437 |
| 5,317,156 | 5/1994 | Cooper et al. | 250/345 |
| 5,331,409 | 7/1994 | Thurtell et al. | 356/437 |
| 5,340,987 | 8/1994 | Eckles et al. | 250/345 |
| 5,381,010 | 1/1995 | Gordon | 250/343 |
| 5,468,962 | 11/1995 | Ohishi et al. | 250/343 |
| 5,477,321 | 12/1995 | Johnson | 356/319 |

FOREIGN PATENT DOCUMENTS

WO89/03028  4/1989  European Pat. Off. .

OTHER PUBLICATIONS

Atmospheric pressure monitoring of trace gasses using tunable diode lasers, D.T. Cassidy and J. Reid, Applied Optics, Apr. 1, 1982, vol. 21, No. 7, p. 1185–1190.

Remote detection of methane with a 1.66–$\mu$m diode laser, Kiyoji Uehara and Hideo Tai, Appplied Optics, vol. 31, No. 6, Feb. 20, 1992, p. 809–814.

Measurements of cross–sensitivity to contaminant gases using a highly–selective optical–fibre–remoted methane sensor based on correlation spectroscopy, Henry O. Edwards and John P. Dakin, SPIE vol. 1587 Chemical, Biochemical, and Environmental Fiber Sensors III (1991), p. 250–257. (Month Unknown).

(List continued on next page.)

*Primary Examiner*—Que T. Le
*Attorney, Agent, or Firm*—Anthony R. Lambert

[57] ABSTRACT

A gas detector, comprising a laser transmitter, a laser receiver, a gas reference cell formed of a sealed encircling wall defining an interior volume, a liquid partially filling the gas reference cell, a reference gas dissolved in the liquid and forming a vapor within the interior volume, at least a portion of the sealed encircling wall being transparent to electromagnetic radiation emitted by the laser transmitter to permit electromagnetic radiation to enter the gas reference cell, traverse a path through the vapor and exit the gas reference cell; and the laser transmitter, laser receiver and gas reference cell being coupled together with light guiding elements to form light paths that pass from the laser transmitter to the laser receiver through the gas reference cell and from the laser transmitter to the laser receiver through a target zone. A method of detecting a target gas, the method comprising the steps directing laser light from a laser transmitter to a laser receiver through a target zone and through a gas reference cell containing a sample of the target gas, wherein the gas reference cell contains a liquid in which the target gas is partially dissolved; detecting light from the laser transmitter that has passed through the target zone and light from the laser transmitter that has passed through the gas reference cell; and analyzing the detected light for the presence of the target gas in the target zone.

14 Claims, 2 Drawing Sheets

OTHER PUBLICATIONS

In Situ and Real–Time Measurement of Methane Concentration in Rice Paddy Field at Okayama University Using Tunable Diode Laser Absorption Spectrometry, Naoki Kagawa, Osami Wada, Xu Hai, Ryuji Koga, Hiroya Sano and Kazayuki Inubushi, Jpn. J. Appl. Phys. vol. 32 (1993) Pt. 1, No. 1A, p. 244–245. (Month Unknown).

Remote detection of gases by diode laser spectroscopy, A. Mohebati and T.A. King, Journal of Modern Optics, 1988, vol. 35, No. 3, 319–324. (Month Unknown).

Remote Sensing of Methane Gas by Differential Absorption Measurement Using a Wavelength Tunable DFBLD, Y. Shimose, T. Okamoto, A. Maruyama, M. Aizawa, and H. Nagai, IEEE Photonics Techndology Letters, vol. 3, No. 1, Jan., 1991, p. 86–87.

Adjoint Spectrum I: an Algorithm to Extract Target Spectra Under Spectral Interferences for Use in On–Line Spectrometry, Moncef Bouzidi, Naoki Kagawa, Osami Wada and Ryuji Koga, Jpn. J. Appl. Phys. vol. 31 (1992) Pt. 3, No. 12A, p. 4071–4080. (Month Unknown).

A Novel Optical Fibre Methane Sensor, J.P. Dakin, C.A. Wade, SPIE vol. 734 Fibre Optics '87: Fifth International Conference on Fibre Optics and Opto–Electronics (1987), p. 254–260. (Month Unknown).

Absorption measurement of $v_2 + 2v_3$ bank of $CH_4$ at 1.33 $\mu$m using an InGaAsP light emitting diode, Kinpui Chan, Hiromasa Ito, and Humio Inaba, Applied Optics, vol. 22, No. 23, Dec. 1, 1983, p. 3802–3804.

Frequency modulation and wavelength modulation spectroscopies: comparison of experimental methods using a lead–salt diode laser, David S. Bomse, Alan C. Stanton, and Joel A. Silver, Applied Optcs, vol. 31, No. 6, Feb. 20, 1992, p. 718–731.

6,121,627

GAS DETECTOR WITH REFERENCE CELL

FIELD OF THE INVENTION

This invention relates to gas detectors, particularly gas detectors which use wavelength modulation spectroscopy to detect gas.

BACKGROUND OF THE INVENTION

Wavelength modulation spectroscopy, such as described in U.S. Pat. No. 5,637,872 and the references cited therein, requires a reference gas absorption cell. The cell has the dual purpose of providing an absorption wavelength reference and an absorption magnitude reference. Typically the reference cell is periodically switched into the beam path. The wavelength spectrometer measures the absorption as the laser wavelength is scanned across the gas absorption line, and the laser center wavelength is adjusted so that absorption occurs at a convenient part of the scan. The peak of the gas absorption might for example be centered on the scan or it may be at the extremities of the scan if an adjacent atmospheric absorption interferes with the gas absorption. The tunable laser is usually a semiconductor diode laser, which may be tuned either using bias current or operating temperature. Because electronic sensitivity changes, with for example electronic drift and offset, the reference and offset gas cell may be used to calibrate the spectrometer each time the cell is switched into the beam path. In this step the peak absorption of the reference cell is recorded and stored. External unknown absorption is then compared with the recorded reference recorded absorption and the external absorption is obtained ratiometrically rather than using an electronic signal level.

In the art, gas absorption cells typically consist of elongated tubes sealed at the ends with thin windows. Etalon interference is well known in wavelength absorption spectroscopy so that reference cell windows must be carefully designed. In one method, described in the aforementioned patent, the windows have a wedge shape with a defined angle so that etalon interference occurs at a frequency outside the sensitivity of the spectrometer. In another method using HF gas, glass windows cannot be used since this gas reacts with the windows. Prior art gas absorption cells used to contain, for example, HF and HCl have been fabricated from gold plated Inconel™ metal with thin sapphire windows bonded onto the tube using fluoridated O-ring seals. Even after careful processing to remove grease and trapped water these cells must be periodically refilled and since the gas concentration in the cell falls with time, usually in an unpredictable manner, these cells cannot be used for ratiometric calibration. Typically, as shown in FIG. 3, very thin glass windows 50, 52 are bonded onto a reference cell tube 48 at an angle to the tube axis 58. A filling port 54 and evacuation port 56 are also provided for filling and emptying the tube 48 with gas 60. An angle of 10° and a window thickness of 0.5 mm are typical. Prior art gas reference cells are difficult to fabricate for the containment of reactive gases such as hydrogen fluoride. This gas is highly toxic and corrosive and is used in aluminum smelters, refineries and other industrial processes.

HF gas in a standard gas absorption cell is very rapidly consumed by the cell. The gas reacts with water vapor released by the cell walls and with the material of the cell walls. In the case of a gas reference cell once a laser interferometer is installed into an industrial facility, servicing requires a service visit by a trained technician who will refill the cell and recalibrate the instrument with an external cell to meet regularity requirements. Such an external calibration cell for reactive gases requires a "flow through" system where gases containing a small concentration of, for example, HF are flushed through the cell until equilibrium is reached. Releasing toxic gas such as HF into an enclosure such as a building is of course not usually possible which makes in situ calibration difficult.

SUMMARY OF THE INVENTION

In accordance with an aspect of the invention, there is disclosed a gas reference cell which does not require refilling with toxic gas so does not require elaborate regularatory recalibration on a period basis. The gas reference cell may also be used for laser wavelength regulation known in the art as "line centering" and for ratiometric calibration of the laser spectrometer.

There is therefore provided in accordance with an aspect of the invention, a gas detector, comprising a laser transmitter, a laser receiver, a gas reference cell formed of a sealed encircling wall defining an interior volume, a liquid partially filling the gas reference cell, a reference gas dissolved in the liquid and forming a vapor within the interior volume, at least a portion of the sealed encircling wall being transparent to electromagnetic radiation emitted by the laser transmitter to permit electromagnetic radiation to enter the gas reference cell, traverse a path through the vapor and exit the gas reference cell; and the laser transmitter, laser receiver and gas reference cell being coupled together with light guiding elements to form light paths that pass from the laser transmitter to the laser receiver through the gas reference cell and from the laser transmitter to the laser receiver through a target zone.

The encircling wall is preferably an integral base and transparent side wall, with a cap opposed to the base. To avoid etalon effects, the gas reference cell may be mounted for rotation about a central axis parallel to the side wall. The gas detector is particularly suited for use when the reference gas is HF, preferably dissolved in an aqueous solution of hydrofluoric acid.

There is also provided in accordance with a method of the invention, a method of detecting a target gas, the method comprising the steps of:

directing laser light from a laser transmitter to a laser receiver through a target zone and through a gas reference cell containing a sample of the target gas, wherein the gas reference cell contains a liquid in which the target gas is partially dissolved;

detecting light from the laser transmitter that has passed through the target zone and light from the laser transmitter that has passed through the gas reference cell; and analyzing the detected light for the presence of the target gas in the target zone.

Analyzing the detected light preferably comprises compensating for temperature controlled variation of concentration of target gas in the gas reference cell. Two methods of temperature variation compensation are provided. In the first, data stored in the analyzer represents change in the light absorption signal from the gas reference cell as the temperature varies. In the second, data stored in the analyzer represents the light absorption signal from the gas reference cell at a specific known temperature. In either case, the actual light absorption signal from the gas reference cell may be adjusted by reference to this data. The invention has particular applicability to toxic gases that are dissolvable in an aqueous solution.

These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which.

DETAILED DESCRIPTION OF PREFERRED EMBODIMENTS

The term light as used in this patent document means electromagnetic radiation of any frequency useful in the detection of gas.

Figure 1:
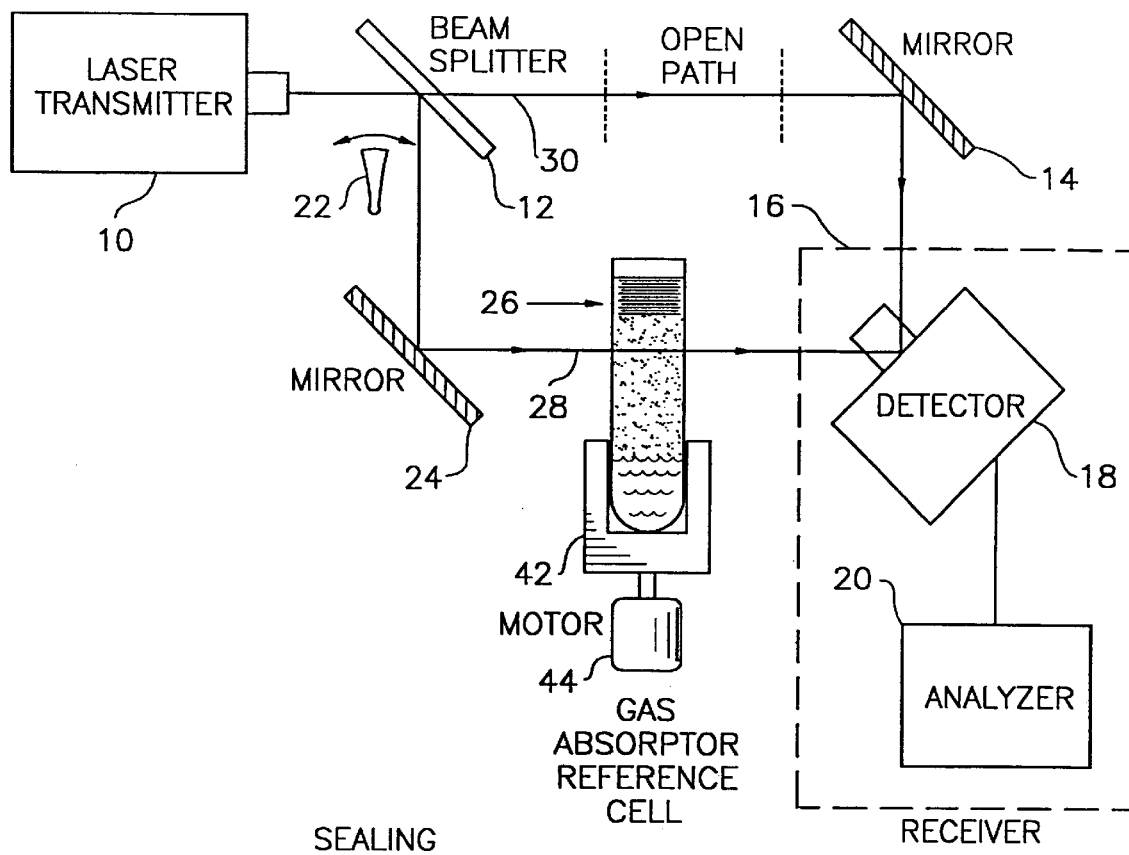
FIG. 1 shows a perspective view of a gas reference cell according to the invention.

The gas reference cell described here is intended for use with a gas detector that includes, as shown in FIG. 1, a laser transmitter 10 and a laser receiver 16. The laser receiver 16 will include a photodetector 18 and an analyzer 20, which analyzes the signal from the photodetector 18 for presence of the target gas in the target zone. The general design of the laser transmitter 10 and laser receiver 16 and the method of wavelength modulation spectroscopy is well known in the art. The laser transmitter 10 and laser receiver 16 are connected by two light paths, which divide at beam splitter 12 and re-combine at photodetector 18 in receiver 16. An open path 30 passes from the beam splitter 16 through a target zone, which may contain the target gas, to a mirror 14 and thence to the photodetector 18. A second path 28 passes from the beam splitter 16 to a mirror 24 and then through gas reference cell 26 to photodetector 18. Light passing to the gas reference cell 26 may be selectively blocked using shutter 22. The light paths 28 and 30 may be defined by other light guiding elements or light guides such as additional mirrors and/or lenses. The gas reference cell 26 may be mounted in a cradle 42 on a turntable 44 to allow the gas reference cell 26 to be rotated about its central axis.

The gas detector shown in FIG. 1 works as follows. Laser light from the laser transmitter 10 is directed to the laser receiver 16 through a target zone and through the gas reference cell 26 which contains a sample of the target gas along with the liquid in which the target gas is partially dissolved. Laser light that has followed both paths is detected at the laser receiver and analyzed at the receiver for the presence of the target gas in the target zone. The general technique of wavelength modulation spectroscopy is well known in the art and need not be described further here. One example of the technique is described in U.S. Pat. No. 5,637,872.

The gas reference cell 26 contains a liquid solution 40 in which the reactive gas is dissolved. In the case of HF, the liquid is preferably a hydrofluoric acid solution in water. The reactive gas forms as a vapor 38 above the solution and remains in a liquid equilibrium. Many reactive gases such as the acids and ammonia will form volatile solutions and would be suitable for this invention. The reference cell 26 is an integral construction of transparent corrosion resistant material forming a sealed encircling wall 32 and preferably has no windows. The sealed encircling wall 32 defines an interior volume. The cell 26 may be sealed with an 'O' ring or, if it is a plastic cell, with a compression seal. The laser beam passes through the wall 32 of the cell 26 and through the vapor 38 above the contained liquid solution 40 which partially fills the interior volume.

It is well known in the art that windows used for wavelength modulation spectrometers must be designed very carefully in order to avoid etalon interference effects. Thus reference cell windows are typically very thin glass held at an angle to the optical axis. The walls of a transparent vessel, of necessity, are not thin or held at a particular angle to the optical axis because they are usually molded or pressure formed and are optically very coarse. A transparent vessel when held in the beam of a wavelength modulation spectrometer hence causes unacceptable interference and the reference gas absorption response is highly distorted and likely to be unusable. However, if an integral gas reference cell is rotated on its axis, which is held at 90° to the optical axis, then a position can be found which reduces the etalon interference to a very small signal level. This technique which is termed "nulling" results because the etalon noise caused by one surface of the cell is cancelled by the noise from the second surface. The set up procedure for an integral gas absorption cell hence simply requires that the cell 26 be placed into the instrument with the instrument recording the reference signal. The reference cell 26 is then rotated, as for example with turntable 44, so that the recorded signal becomes undistorted by the cell walls 32. While the cell 26 may be rotated by hand, using turntable 44 permits automatic operation. This process usually results in the power striking the light detector 18 to change significantly. Open path wavelength modulation spectrometers, however, are designed so that detected light level variations caused by optical deterioration or atmospherics are accounted for in the receiver circuitry and do not influence the instrument reading. Changes in light level caused by nulling the interference from an integral gas absorption cell are consequently not important.

An advantage of using a liquid solution—gas interface as a gas source is that gas losses associated with reaction or gas absorption into the material of the cell 26 is constantly replenished by the equilibrium established between the gas 38 and solution 40. Furthermore the gas concentration can easily be adjusted to a suitable level simply by changing the concentration of active material in the solution 40. A disadvantage of using a gas-solution interface is that the vapor pressure of gas above the solution changes with temperature. A working HF detector is for example required to operate over an ambient temperature variation of −40° to +65°, which causes a very large change in gas vapor pressure. The vapor pressure can easily be determined using the wavelength modulation spectrometer to measure the gas concentration in the cell which leads to a method of temperature correction. The instrument is calibrated at 20° C. and the gas concentration, at this temperature, in the reference cell can be determined. Raising or lowering the ambient temperature results in a measured change of the gas cell gas concentration and a graph of gas cell temperature versus concentration may be found. This graph is used to create a computer look-up table, which is used to correct the instrument readings that are made with the instrument at elevated or lowered temperature. The computer look-up table is stored in a memory, which forms a part of conventional analyzers. For example at elevated temperature the gas cell concentration is raised. A ratiometric comparison between the gas cell signal and an external unknown gas concentration will hence change. An instrument calibrated for 20° C. operation would hence underestimate the external gas concentration unless a correction is applied. This correction is provided by the look-up table stored in the analyzer.

A second alternative temperature compensation method requires that the absolute reference cell signal is periodically recorded and compared with a computer stored reference signal made for 20° C. operation. Any change results in a non unity ratio of these two signals. This ratio may then be used to correct external unknown gas absorption signals. If the reference cell signal increases for example, due to temperature increase, a ratio of greater than unity will be recorded. As described earlier, this results in an underestimation of external unknown gas concentration if no correction is applied. In this case, the correction is made simply by multiplying the external signal by the reference signal ratio. The second method has the advantages that temperature equilibrium is not necessary and it also provides an electronic method of checking the status of the absorption cell for possible failure, which is necessary for regularatory quality assurance. Measurement of a known external gas cell for an instrument whose temperature is varied over the full environmental range has shown that the second method results in a calibration variation of less than 5% over the full operating environmental temperature range. The second method has the disadvantage that it depends to some extent on the electronics of the analyzer, which may not be constant with time.

The advantages of the use of the disclosed gas reference cell over prior art absorption cells are hence as follows. No deterioration of gas absorption occurs over time so that expensive refilling and recalibration procedures in the field are unnecessary. The integral gas absorption cell is very simple and inexpensive since no special windows or sealing methods are needed. The integral gas absorption cell, unlike prior art gas reference cells, can be used for both laser line centering and ratiometric determination of external gas concentration. Temperature calibration of the gas reference cell is not required when the gas detector is used in a temperature constant oven, but such a device is expensive and awkward to operate and thus is preferably not used.

Figure 2:
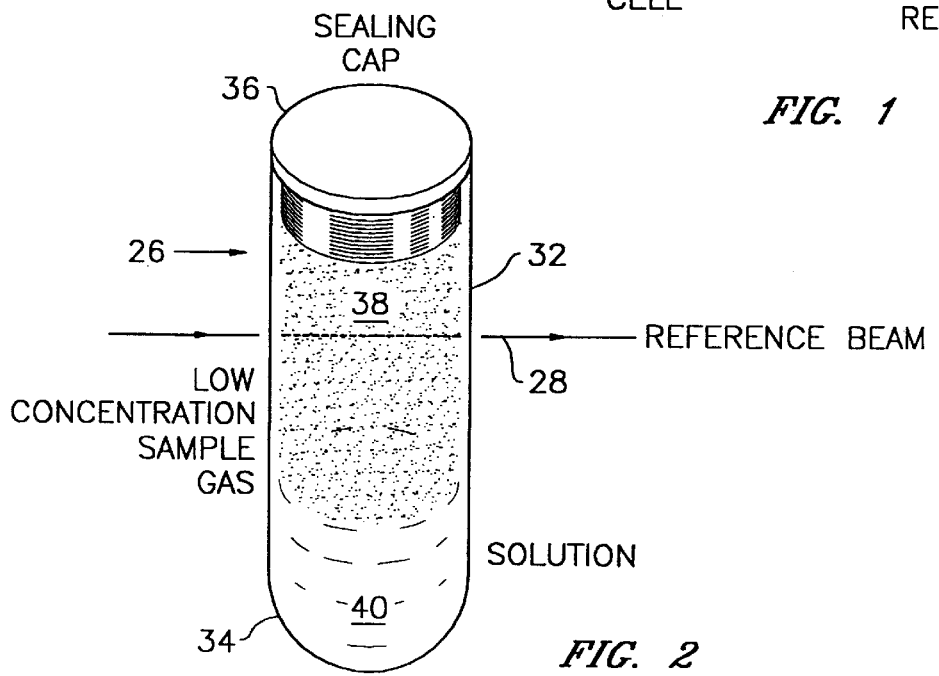
FIG. 2 is a schematic showing an open path wavelength modulation spectrometer using a gas reference cell according to the invention.
Figure 3:
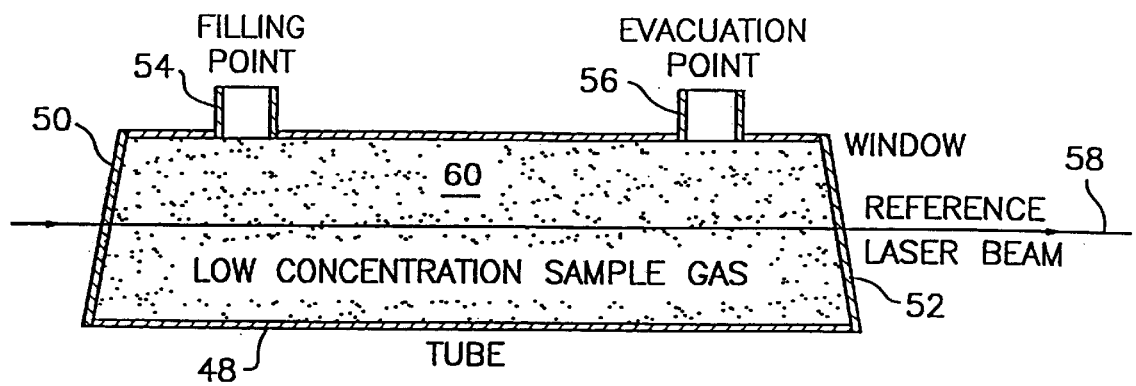
FIG. 3 shows a prior art reference cell.
Figure 4:
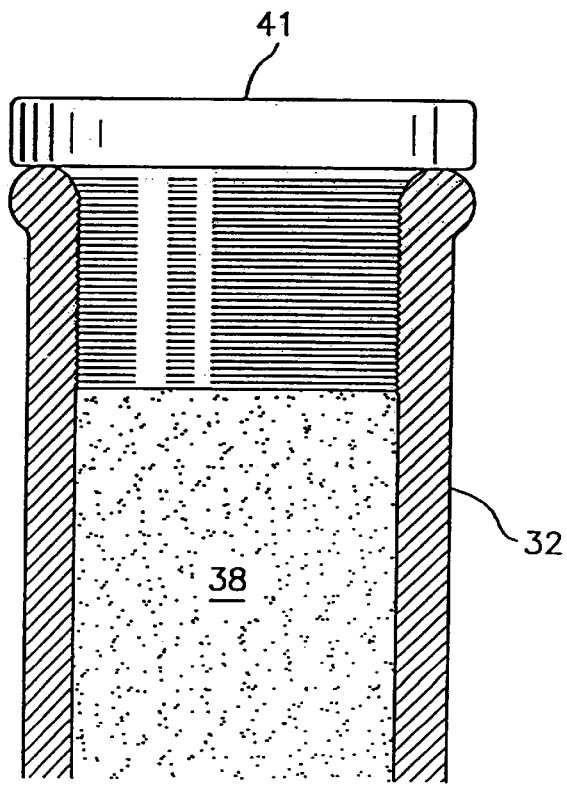
FIG. 4 shows design of a cap for a gas reference cell according to the invention.

An exemplary integral absorption cell 26 suitable for a HF wavelength modulation spectrometer is shown in FIGS. 2 and 4. This cell consists of a 1 cm diameter TEFLON™ tube sealed at one end and with a cap 36 at the other end. The cap 36 may for example be a crush plastic seal 41 screwed into threads at the top of the encircling wall 32 of the gas reference cell 26. HF gas and hydrofluoric acid both react with glass so that plastic, preferably TEFLON™ plastic, is necessary. TEFLON™ is sufficiently transparent at the absorption wavelength of 1321 nm to be suitable for an absorption cell. The cell 26 shown in FIG. 2 is the type used in centrifugal analysis so that the construction is rugged enough to maintain its integrity under industrial environmental conditions. A tube of square or rectangular cross section and greater or smaller absorption path would also be suitable. About 0.5 cm$^3$ (cl.) of hydrofluoric acid is added to the absorption cell 26 and the beam passes through the cell 26 above the acid 40. A further advantage of TEFLON™ is that condensation of water on the tube walls 32 does not occur under varying temperature conditions and droplets of acid, which splash onto the walls 32 during movement of the instrument, flow back into the acid 40. Hence, accidental obstruction of the reference beam, which condensation and droplets could cause, does not occur. The HF density above the acid 40 may be varied by changing the acid concentration so that path lengths of different size may be accommodated with an optical absorption suitable for the instrument. For a path length of 1 cm, a 35% hydrofluoric acid solution is optimum. Lifetime of many years is expected. Other exemplary toxic gases with which the reference cell is believed to work are HCl, HCN, HBr and NH$_3$, with the gas being dissolved in an aqueous solution (eg hydrochloric acid, hydrocyanic acid etc).

The cell 26 need not be cylindrical or even have a simple form. For example, the liquid 40 may be in a first enlarged portion of a container with a narrow neck connecting the first enlarged portion with a second enlarged portion. Not all of the wall 32 need be transparent but it simplifies construction if it is. A tube, formed of an integral side wall and base, with a threaded cap at the end opposed to the base, is simply constructed.

A person skilled in the art could make immaterial modifications to the invention described in this patent document without departing from the essence of the invention that is intended to be covered by the scope of the claims that follow.

The embodiments of the invention in which an exclusive property or privilege is claimed are defined as follows:

1. A gas detector, comprising:
    a laser transmitter;
    a laser receiver;
    a gas reference cell formed of a sealed encircling wall defining an interior volume;
    a liquid partially filling the gas reference cell;
    a reference gas dissolved in the liquid and forming a vapor within the interior volume;
    at least a portion of the sealed encircling wall being transparent to electromagnetic radiation emitted by the laser transmitter to permit electromagnetic radiation to enter the gas reference cell, traverse a path through the vapor and exit the gas reference cell; and
    the laser transmitter, laser receiver and gas reference cell being coupled together with light guiding elements to form light paths that pass from the laser transmitter to the laser receiver through the gas reference cell and from the laser transmitter to the laser receiver through a target zone.

2. The gas detector of claim 1 in which the encircling wall is made of material that does not react with the reference gas.

3. The gas detector of claim 2 in which the encircling wall comprises an integral base and side wall.

4. The gas detector of claim 3 in which the encircling wall comprises a cap opposed to the base.

5. The gas detector of claim 2 in which the gas reference cell is movably mounted for varying the path traversed by the electromagnetic radiation through the interior volume.

6. The gas detector of claim 3 in which the side wall is transparent.

7. The gas detector of claim 2 in which the reference gas is HF.

8. The gas detector of claim 7 in which the liquid is an aqueous solution of hydrofluoric acid.

9. A method of detecting a target gas, the method comprising the steps of:
    directing laser light from a laser transmitter to a laser receiver through a target zone and through a gas reference cell containing a sample of the target gas, wherein the gas reference cell contains a liquid in which the target gas is partially dissolved;
    detecting light from the laser transmitter that has passed through the target zone and light from the laser transmitter that has passed through the gas reference cell; and
    analyzing the detected light for the presence of the target gas in the target zone.

10. The method of claim 9 in which analyzing the detected light comprises compensating for temperature controlled variation of concentration of target gas in the gas reference cell.

11. The method of claim 10 in which compensating for temperature controlled variation of concentration of target gas in the gas reference cell comprises storing in the analyzer data representing variation of absorption of light arriving from the gas reference cell at the photodetector as the temperature of the vapor in the gas reference cell varies.

12. The method of claim 10 in which compensating for temperature controlled variation of concentration of target gas in the gas reference cell comprises storing in the analyzer data representing absorption of light arriving from the gas reference cell at the photodetector at a fixed temperature and adjusting data obtained with the gas reference cell at a different temperature using the first mentioned data.

13. The method of claim 9 further comprising moving the gas reference cell to reduce interference due to etalon effects.

14. The method of claim 13 in which moving the gas reference cell comprises rotation of the gas reference cell about a central axis.

* * * * *